US012000821B2

(12) United States Patent
Khonsari et al.

(10) Patent No.: US 12,000,821 B2
(45) Date of Patent: Jun. 4, 2024

(54) FLUID MONITORING

(71) Applicants: Michael M. Khonsari, Baton Rouge, LA (US); Lijesh Koottaparambil, Baton Rouge, LA (US)

(72) Inventors: Michael M. Khonsari, Baton Rouge, LA (US); Lijesh Koottaparambil, Baton Rouge, LA (US)

(73) Assignee: Bd. of Supervisors of La. St. Univ. & A&MCollege, Baton Rouge, LA (US)

( * ) Notice: Subject to any disclaimer, the term of this patent is extended or adjusted under 35 U.S.C. 154(b) by 283 days.

(21) Appl. No.: 17/344,464

(22) Filed: Jun. 10, 2021

(65) Prior Publication Data

US 2021/0389295 A1 Dec. 16, 2021

Related U.S. Application Data

(60) Provisional application No. 63/037,421, filed on Jun. 10, 2020.

(51) Int. Cl.
*G01N 33/28* (2006.01)
*F16N 29/00* (2006.01)
*G01N 33/30* (2006.01)

(52) U.S. Cl.
CPC ......... *G01N 33/2888* (2013.01); *F16N 29/00* (2013.01); *G01N 33/30* (2013.01); *F16N 2200/00* (2013.01)

(58) Field of Classification Search
CPC .... G01N 33/2888; G01N 33/30; F16N 29/00; F16N 2200/00
See application file for complete search history.

(56) References Cited

U.S. PATENT DOCUMENTS 8,531,672 B2 * 9/2013 Takahashi ............... G01N 3/56
356/442
2019/0234463 A1 * 8/2019 Lugt .................. F16C 33/6633
2021/0389295 A1 * 12/2021 Khonsari ............... F16N 29/00

FOREIGN PATENT DOCUMENTS

| CN | 108008119 A | * | 5/2018 | ......... G01N 33/2888 |
| JP | 2020012690 A | * | 2/2020 | ............ G02B 1/115 |
| JP | 2020200892 A | * | 12/2020 | |
| JP | 2022052591 A | * | 4/2022 | |
| WO | WO-2014167503 A1 | * | 10/2014 | ............ G01N 11/00 |
| WO | WO-2017007333 A1 | * | 1/2017 | ............ E21B 19/06 |

OTHER PUBLICATIONS

Rezasoltani, A. Khonsari, M. M. On the Correlation between Mechanical Degradation of Lubricating Grease and Entropy, Tribology Letters 60 (1), (2015): 1-4.

(Continued)

*Primary Examiner* — Francis C Gray
(74) *Attorney, Agent, or Firm* — Edel Patents LLC; John B. Edel

(57) ABSTRACT

Methods of evaluating mixing are disclosed relating to the preparation and mixing of materials. Materials prepared may transition from heterogeneous mixtures to homogenous mixtures while the current of a motor is monitored. Quantities relating to the rate of change of power or the rate of change of entropy may be calculated in evaluating the sufficiency of mixing. Methods of evaluating lubricant degradation are also disclosed.

19 Claims, 10 Drawing Sheets

(56) References Cited

OTHER PUBLICATIONS

Rezasoltani, A., Khonsari M. M. An engineering model to estimate consistency reduction of lubricating grease subjected to mechanical degradation under shear. Tribology International 103 (2016): 465-474.

Rezasoltani, A., Khonsari M. M. Mechanical degradation of lubricating grease in an EHL line contact. Tribology International 109 (2017): 541-551.

Lijesh, K. P., Khonsari M. M. On the Assessment of Mechanical Degradation of Grease Using Entropy Generation Rate. Tribology Letters 67, No. 2 (2019): 50.

Zhou, Y., Bosman R., Lugt P. M. A model for shear degradation of lithium soap grease at ambient temperature. Tribology transactions 61 (1), (2018): 61-70.

\* cited by examiner

FLUID MONITORING

This application claims the benefit of provisional application No. 63/037,421 filed on Jun. 10, 2020 and entitled Fluid Monitoring.

Embodiments described herein may provide information about progress of mixing operations and other embodiments described herein may be useful in evaluating the useful life of lubricants. Methods and devices described herein may be used in the monitoring of the degradation of various fluids. Certain methods and devices disclosed herein relate to grease and other lubricants.

DETAILED DESCRIPTION

Example Set 1

Degradation

Figure 1:
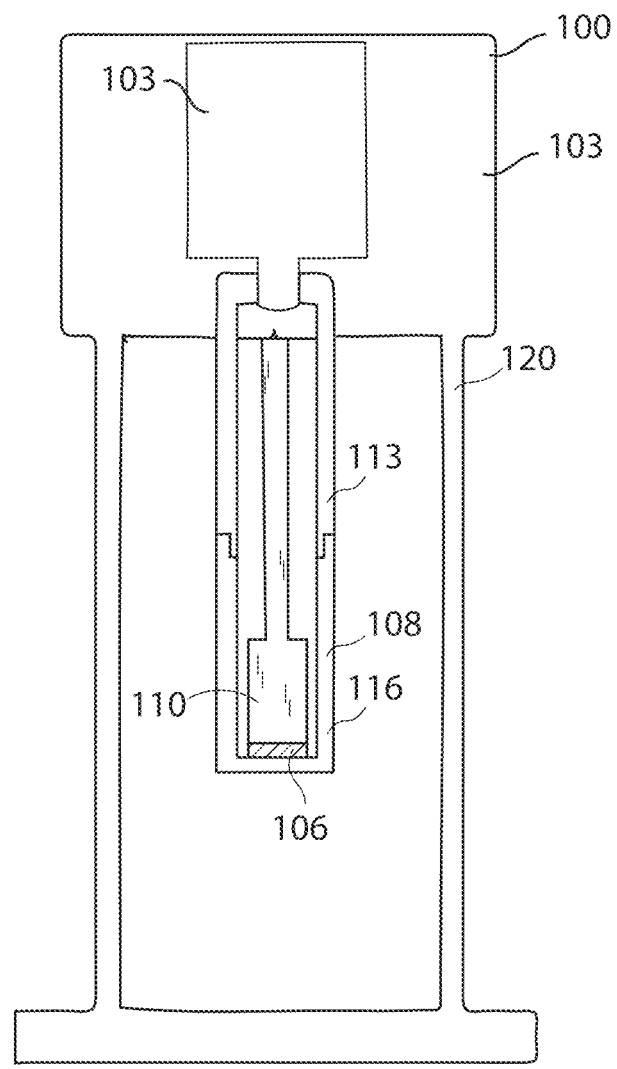
FIG. 1 depicts a testing rig.

In contrast to lubricating oils, grease is expected to possess good sealing properties require minimum maintenance, tolerate contamination, and function without requiring recirculating arrangements. Due to these beneficial properties, grease is employed in bearings, gears, slideways, and the like. However, the rheological properties of in-service grease tend to degrade with time. Hence, determining the rate of degradation has prodigious importance to the industry for scheduling re-lubricating intervals to avoid loss of efficiency and even component failure.

The causes of grease degradation can be chemical, physical, or both. A methodology for determining the degradation due to mechanical shearing, which is classified as a physical degradation is evaluated herein. One measure of mechanical degradation is by means of a penetrometer, where a cone assembly is released and allowed to drop freely into worked or degraded grease for 5±0.1 s. Based on the penetration depth value, the grease is designated with an NLGI grade between 000 to 6, representing grease from the lowest to highest viscosity (from lightest to heaviest consistency). However, this method generally requires a fairly large grease sample (0.45 kg, 1 lb) to be collected periodically from a component for testing. This is a time-consuming process and not easily applicable for real-time monitoring since the operation of the machine must be halted during the sample extractions. Further, the applied shearing rate conditions are typically fixed, making it difficult to induce different degradation rates for empirical studies.

The entropy generated during the shearing of grease is due to the friction work imparted by the surfaces in relative motion. During shearing, the grease mechanically degrades as a result of breaking the chains, separation of base oil, etc. Prolonged mechanical degradation affects the grease consistency, thus altering this NLGI grade.

Mechanical degradation of a grease may be measured by monitoring the time it takes for the consistency of a higher grade grease (e.g., Grade 1) to reach a lower grade grease (e.g., Grade 00). This approach provides a useful method for determining the grease life and informing the operator to replace the grease. Methods may be implemented using a precision torques sensor, an appropriate data acquisition system and a voltage measuring analog system with the necessary software. Such requirements limit the full-fledged implementation such a method in the industry.

In certain embodiments, a Grease Degradation Monitoring Unit (GDMU) may be used to assess the mechanical degradation of grease through the laws of thermodynamics. The embodiments may be easier and more practical in industrial settings.

The reduction in the rheological properties of grease, during its shearing, may be correlated to the power associated with the motor. A test setup to shear grease at the desired shear rate was developed, and a series of experiments at different rotational speeds was performed for NLGI grade 1 grease. During the shearing of grease, the power consumed by the motor was continuously monitored using the GDMU.

In the present work, an NLGI grade 1 lithium-complex based greases were utilized to demonstrate the efficacy of the GDMU. The properties of the considered grease are provided in Table 1. A custom-built setup was developed to shear the grease at the desired rotational speeds by employing a small amount of grease.

TABLE 1

| | | Grease properties | | |
|---|---|---|---|---|
| Grease | NLGI Grade | Appearance, color | Thickener | Viscosity @ 40° C. (m²/s) × 10⁻⁶ |
| XHP 221 | 1 | Soft, Blue | Li-Complex | 220 |

The testing rig 100 is shown in FIG. 1. In this setup, the grease sample 106 is sheared between the rotating part 108 and the stationary cylinder 110. The rotating part has a top half 113 and bottom rotating cylinder 116. The top half is connected to the motor 103, while the bottom half facilitates the shearing of grease with respect to the stationary surface. The gap between the bottom surface of the stationary half and the rotating part is 1.5 mm. The diameter of the stationary surface is 50 mm Therefore, the volume of the grease employed is $2.944 \times 10^{-6}$ m³. Support structure 120 supports the testing rig.

Figure 2:
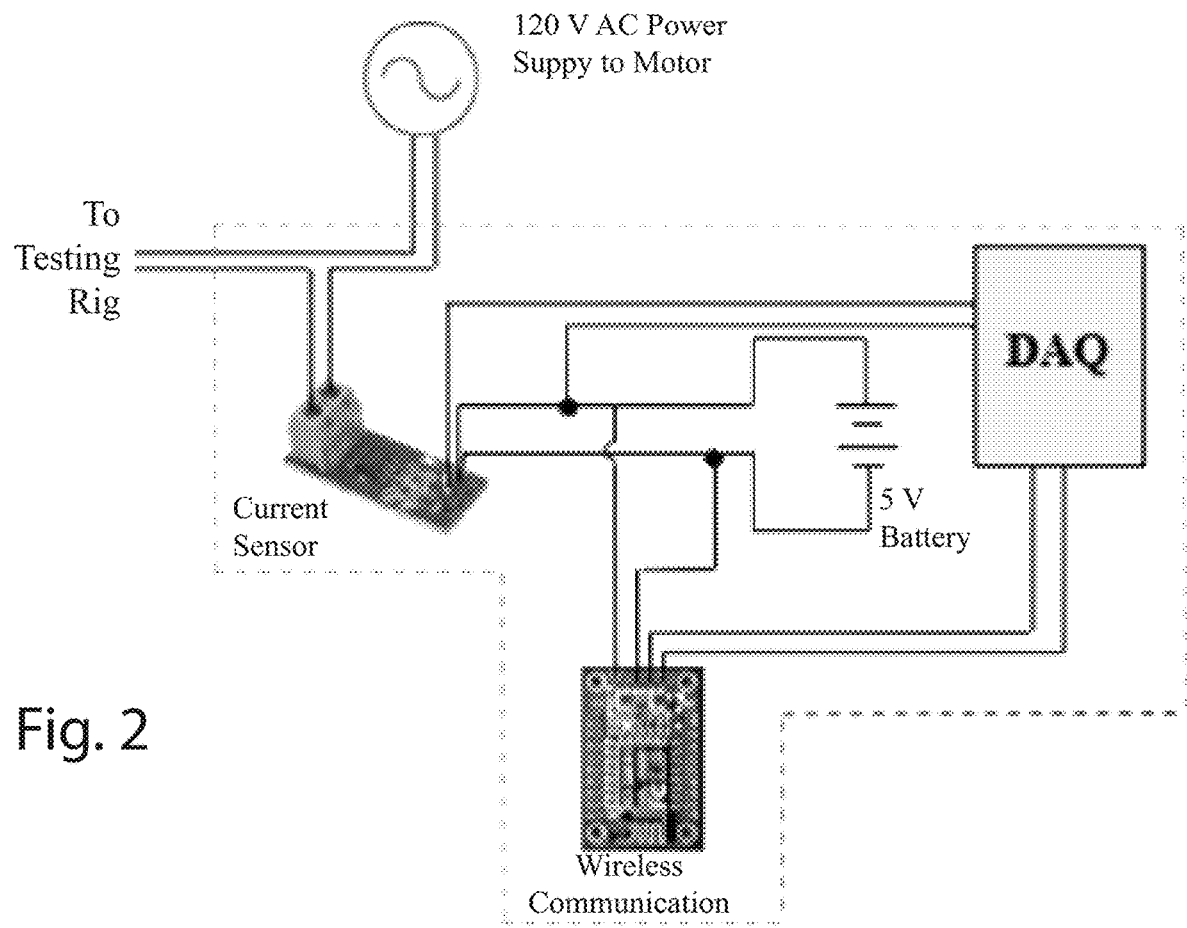
FIG. 2 depicts monitoring unit connections.

The desired motor speed was set and maintained using a controller. The setup is connected to a computer using an RS-232 connection. The speed of the motor is controlled by using the computer. The schematic representation of the connection of the grease shearing setup to the GDMU is provided in FIG. 2.

The power supply of the setup is connected to the current sensor, and the sensor is in turn connected to a data acquisition setup (DAQ). The acquired data are transferred to a laptop pc or smartphone using a wireless network. The 5 V supply to the sensors is provided using a battery.

Figure 3:
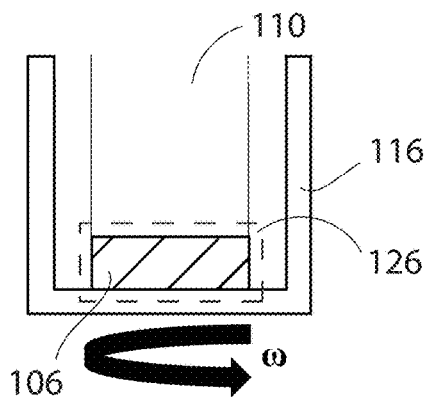
FIG. 3 depicts grease in a testing rig.

The schematic representation of the setup and the control volume 126 is provided in FIG. 3. The grease sample 106 is placed between the stationary cylinder 110 and bottom rotating cylinder 116 and is sheared by rotating the cylinder at an angular speed of ω for shear rate $\dot{\gamma}$. This provides work W on the grease due to friction. Heat is conducted into the contact surfaces in a closed system environment as there is no transfer of matter across the boundary of the control volume.

Now, for a closed local thermodynamic equilibrium (LTE) system, the entropy generation rate per unit volume $\dot{s}_{g,vol}$ can be determined by Eq. (1) assuming that the grease is experiencing only mechanical degradation without appreciable temperature rise $$\dot{S}_{g,vol} = \frac{\tau \cdot \dot{\gamma}}{T} \quad (1)$$

where T is the shear stress, $\dot{\gamma}$ is the shear rate and T is the operating temperature. For the considered setup and operating conditions, the temperature and volume can be considered constant. Letting the parameter a represent the product of the volume of grease vol and temperature, Eq. (1) yields:

$$\dot{S}_{g,vol} = \alpha \cdot \tau \cdot \dot{\gamma} \cdot vol \quad (2)$$

Note that $\tau \cdot \dot{\gamma} \cdot vol$ has the units of watts (W) and represents power P. Based on this description, Eq. (2) can be written as:

$$\dot{S}_{g,vol} = \alpha \cdot P \quad (3)$$

From Eq. (3) it can be concluded that for a constant volume of grease and temperature, the entropy generation rate per unit volume can be suitably correlated to the power consumed.

Power can also be determined by measuring the current and voltage of the system. In the developed setup, the power required to shear the grease at the desired speed is the sum of the power required to rotate the motor and to shear the grease. Therefore, the power consumed by the setup for only shearing the grease is determined by calculating the difference between the total power consumed and the power consumed by the setup without grease. For this purpose, the system is run initially without grease at the desired rotating speed and the power consumed is monitored. Next, the system is operated with the grease sample at the same rotating speed and power consumed is recorded. From the recorded power values, the power required to shear the grease is determined by calculating the difference.

The developed setup employs an alternating current (AC) motor for shearing the grease and the power P of the variable speed AC motor during the shearing operation is determined using Eq. (4)

$$P = V \cdot (I_i - I_0) \cdot \cos\phi \quad (4)$$

where $I_i$ is the instantaneous value of the acquired current, V is the voltage which is considered as a constant value of ~120 V, and $\phi$ represents the phase angle between the voltage and current. $I_0$ is the current consumed by the setup without grease and is determined by operating the rig without grease. The phase angle $\phi$ can be determined by measuring the angle between the resistance R and impedance Z of the motor, as given in Eq. (5):

$$\phi = \cos^{-1}\left(\frac{R}{Z}\right) \quad (5)$$

The resistance of the motor was determined by measuring the resistance of the winding using a digital multi-meter, and impedance was calculated from the ratio of voltage and current consumed by the motor at their respective operating conditions.

Experiments were performed with and without the NLGI grade 1 grease at three rotational speeds: 100, 250, and 500 rpm. The current values obtained at all the three rotational speeds for 3,000 s without grease are plotted in FIGS. 4 and 5. The current drawn when running without grease was 0.165 A and its value increased linearly with the rotational speed. The following curve-fit relationship was used to determine the current requirement for this set up without grease at different speeds.

$$I = 0.165 + 0.00012 \cdot rpm \quad (6)$$

To determine the current consumed during shearing, experiments were repeated by applying the grease to the bottom of the stationary part and the rotating bottom part. Initially, the experiments were performed at 100 rpm, and the current values were recorded. The grease on the bottom of the stationary part after shearing at 100 rpm for an hour clearly revealed that grease was uniformly sheared during the experiment. The measured current values during the shearing at 100 rpm are plotted in FIG. 6. Close examination of this figure shows that there are four regions: (i) Region I—current obtained by operating the system without grease, (ii) Region II—a non-uniform variation of the current for only a short period of time, (iii) Region III—running-in region, and (iv) Region IV—steady-state behavior.

Figure 6:
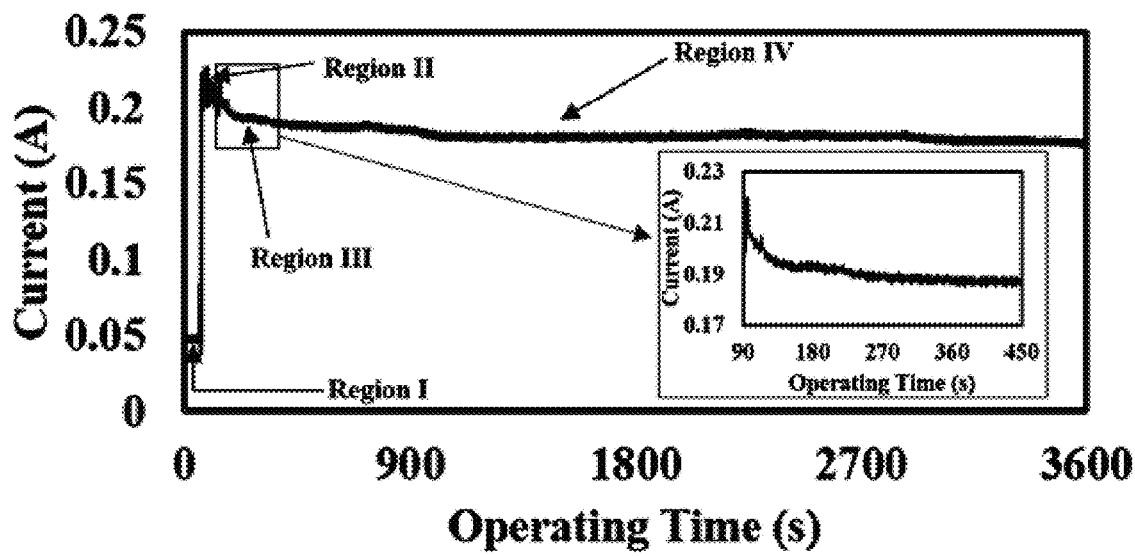
FIG. 6 depicts current values from shearing grease.

The inset of Region III in FIG. 6 shows a magnified picture of the transient region. The variation in the current values in Region II may be due to the variation caused by the non-uniform spreading of grease for ~40 s. Once the grease is uniformly distributed, Regions III and IV are observed. It is noted that the grease itself exhibits a brief transient behavior initially before the process becomes steady.

Figure 7:
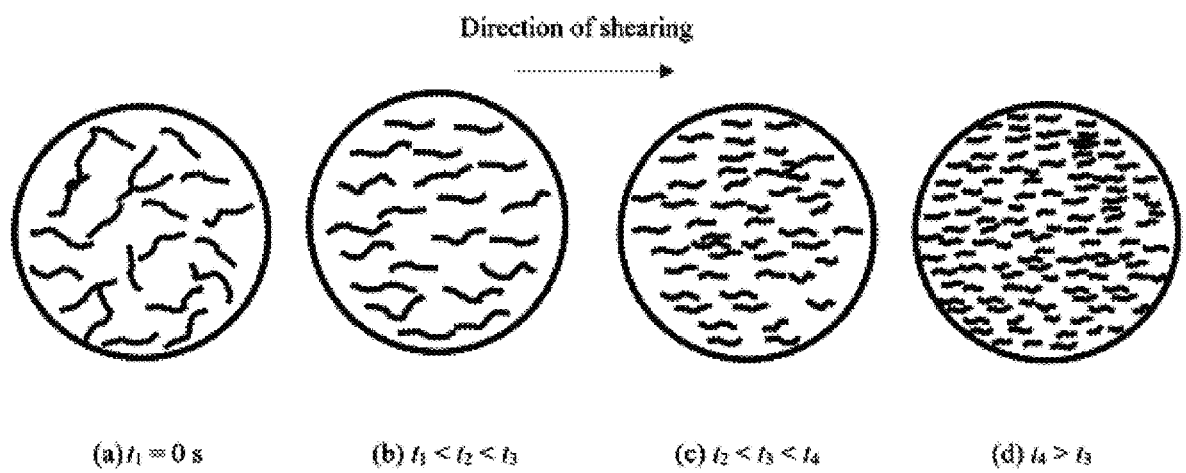
FIG. 7 depicts grease degradation.

The continuous degradation of grease with time shown in FIG. 6 was due to the alignment of chains in the direction of shearing and breakage of the thickener chains in the carrier oil, as schematically shown in FIG. 7. With the breakage of the thickener's chains, the grease became less viscous, but the viscosity still remained higher than that of the carrier oil. The reduction in the viscosity of the grease with time imparted lower shear stress on the rotating surface, and thereby reduced the current drawn by the motor.

Figure 4:
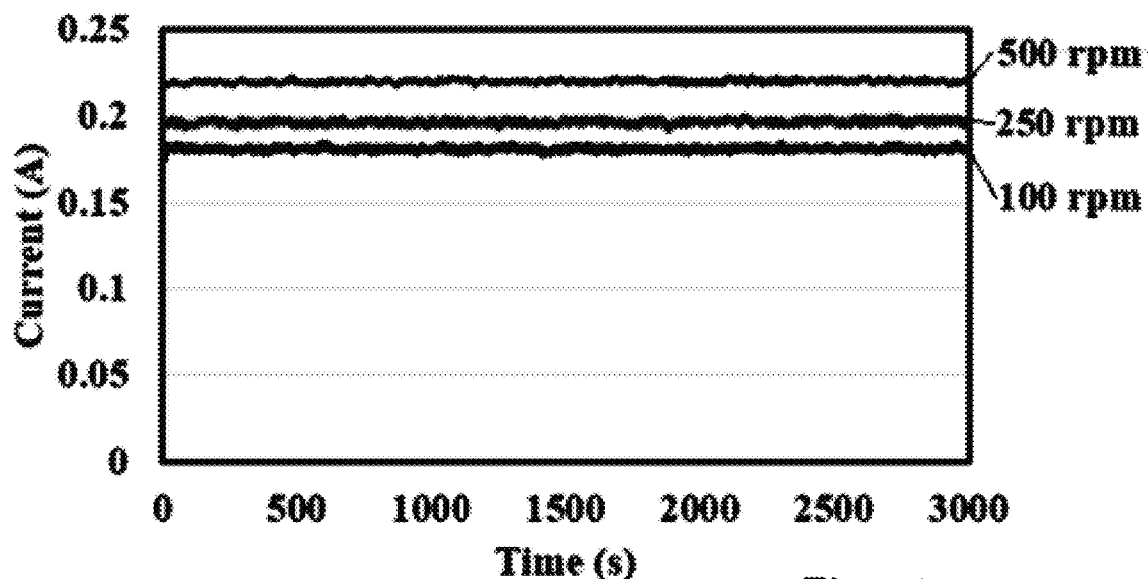
FIG. 4 depicts current values from testing without grease.
Figure 5:
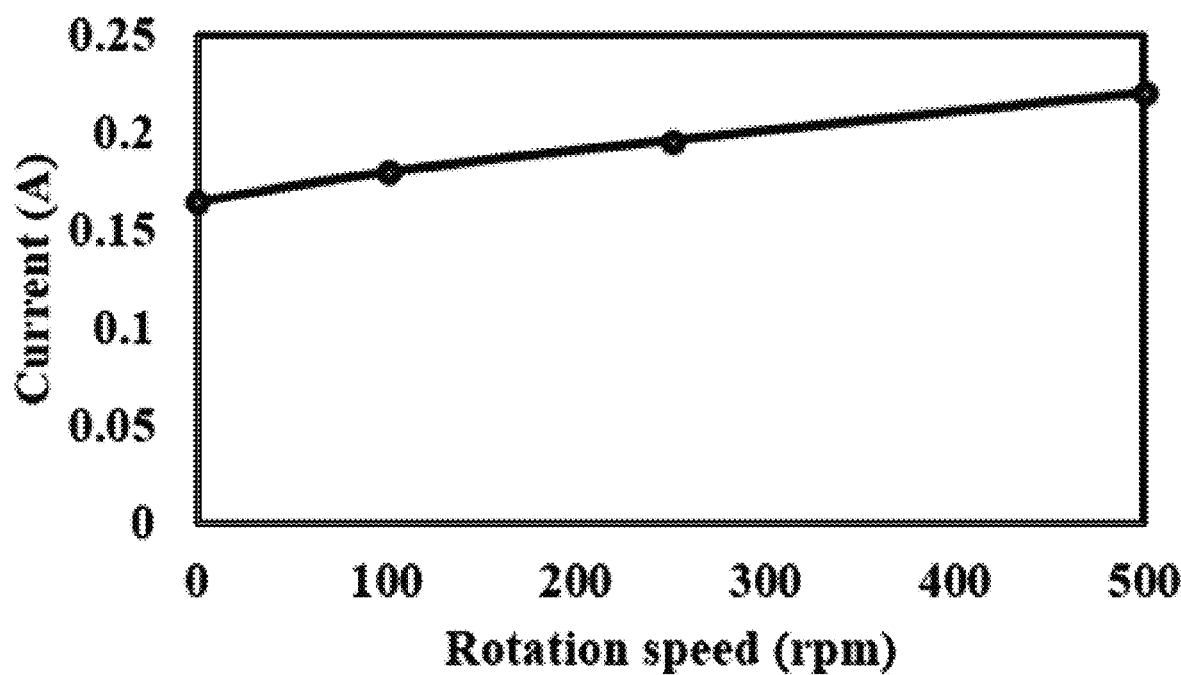
FIG. 5 depicts current values from testing without grease.

Referring again to FIG. 6, it was observed that the value of the current in the steady-state region (I) was greater than that obtained from the setup without grease ($I_0$) (see FIG. 4). The difference in the current values represented the current required to shear the grease.

Figure 8:
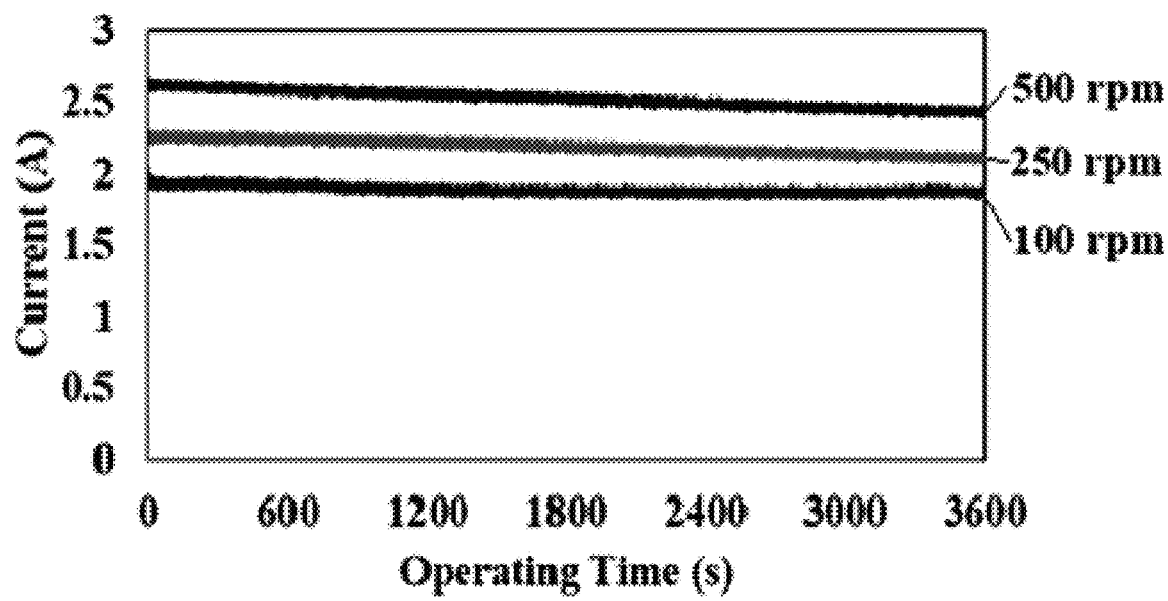
FIG. 8 depicts current values from shearing grease.

Insofar as degradation is concerned, the short period associated with the running-in is less important if one is interested in the long-term operation of a component. Therefore, in the following studies, the steady-state current values were considered for determining the degradation of grease. The change in the current when operating at 100, 250, and 500 rpm is provided in FIG. 8. Now, comparing FIG. 8 and FIG. 4, it can be observed that the current values acquired from the setup with the presence of grease were more than the values of the current recorded without grease.

Figure 9:
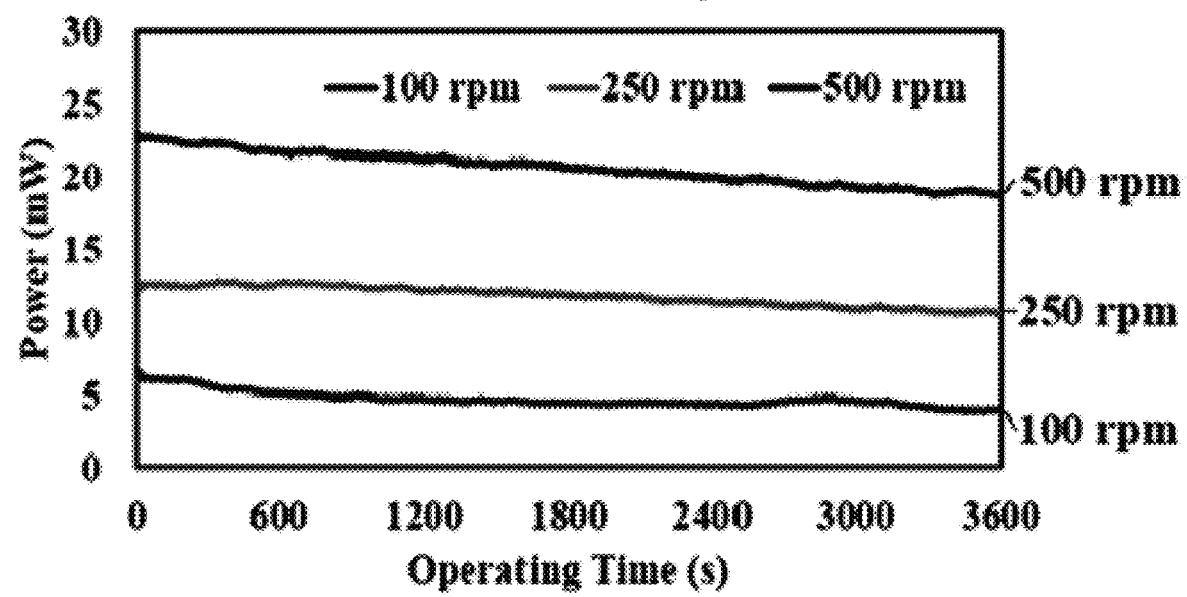
FIG. 9 depicts calculated power.

Using the recorded current values, the consumed power was calculated for different rotational speeds using Eq. (4) and plotted in FIG. 9.

The values of current continuously reduced with time. Therefore, predicting the useful life of the grease in practice may be challenging. A deterministic method of quantifying the degradation of grease in terms of entropy generation may be used. An operator may need to replace grease in an application if its consistency decreases enough to drop its NLGI's grade to a lower value. The severity of the reduction in consistency should be judged by the practitioner's experience and the application. Following the same logic, in the present work, the values of the current drawn by the motor were employed to determine the degradation of the grease. For this purpose, the following steps were taken:

Step 1: Experiments were performed for a higher NLGI grade grease at a desired rotational speed, and the real-time current values were recorded.

Step 2: The experiment was repeated for a lower NLGI grade grease, and their starting current value was recorded and considered as the threshold value.

Step 3: Using the curve fit method, the variation in the current values was extrapolated to determine the time to reach the initial current value of the lower grade grease.

Figure 10:
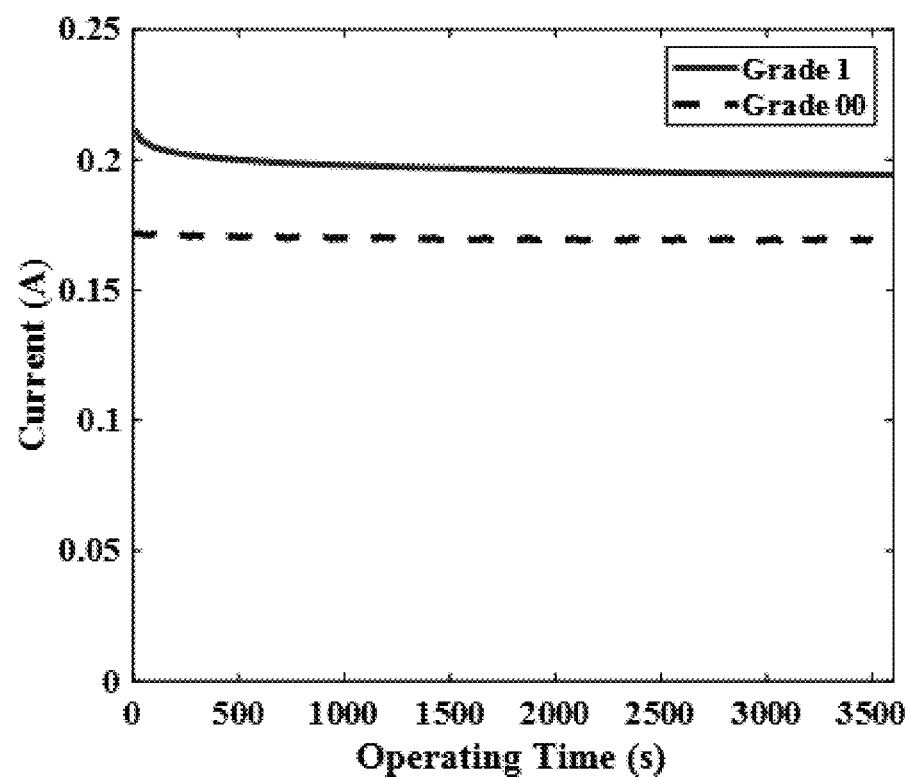
FIG. 10 depicts results of a curve fit calculation.

To demonstrate the efficacy of the proposed methodology, NLGI grade 1 grease was considered to be the appropriate grade grease for the machine to run efficiently. It was assumed that if the prolonged degradation by shearing caused it to drop to NLGI grade 00, then it would be necessary to replace the grease. For Step 1, the current value with time for NLGI grade 1 at 100 rpm, plotted in FIG. 6, was considered. For Step 2, the experiment was repeated with a lower grade grease, i.e. NLGI grade 00 at 100 rpm, and the current values were recorded and plotted in FIG. 10. From this figure, it can be observed that the current values were almost constant at 0.172 A.

Referring to FIG. 6, the variation of the current values with time followed the power curve fit equation provided in Eq. (7).

$$I = At^B + C \tag{7}$$

Using the regression method, the coefficients A, B, and C, depicting the variation of current with time for NLGI grade 1, were determined to be 0.3, −0.014 and 0.0932, respectively. The current values obtained from the curve fit equation were plotted in FIG. 10. Now, Eq. (7) was extrapolated by incrementing the value of time t and the value of t for which the value of I=0.172 A was determined to be t≈$10^7$ s (approximately 4 months of continuous operation).

The method described may serve as a deterministic procedure for determining the degradation of grease using a small sample of grease and employing an analogy between a thermodynamic principle and an electrical system. Through mathematical derivation, it was established that for a constant temperature and volume of grease, the entropy generation rate was proportional to the power generated by the system. Power generated in the system could be estimated by measuring the current and voltage drawn by the driving motor of the system.

From the obtained results it was observed that the power drawn by the motor effectively characterized the degradation of grease at different rotational speeds.

Example Set 2

Grease Kettle

Figure 11:
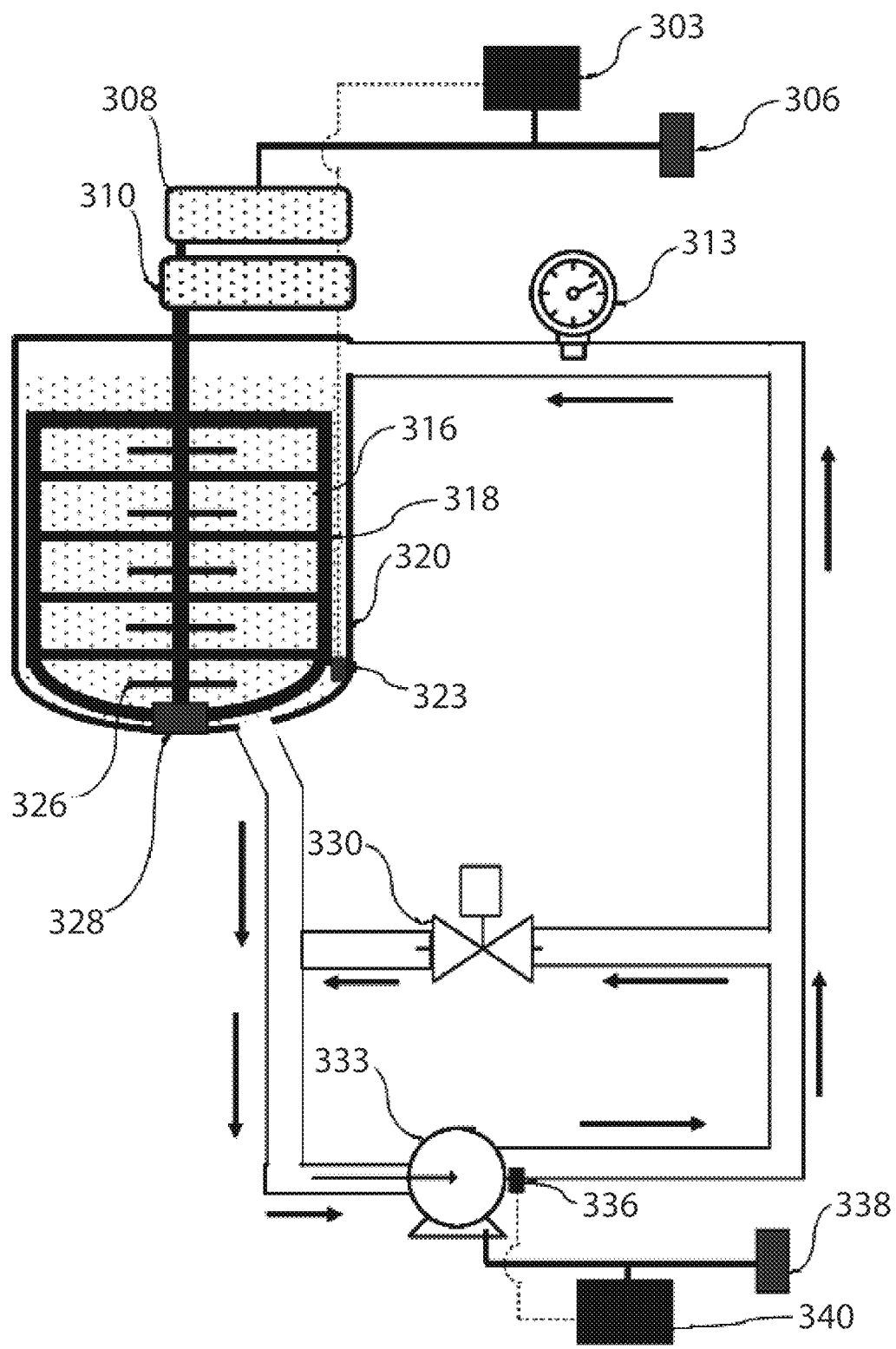
FIG. 11 depicts a grease kettle.

As depicted in FIG. 11, a grease kettle may include a first monitoring unit 303, a first power supply 306, a breaker bar drive 308, a scraper drive 310, a pressure indicator 313, grease 316, a scraper 318, a container 320, a container thermocouple 323, breaker bars 326, a bushing 328, a V-notch valve 330, a gear pump 333, a pump thermocouple 336, a second power supply 338, and a second monitoring unit 340.

In a grease-production kettle, thickeners, oil, and additives are mixed using scrapers and a braker bar connected to counter-rotating gear motors. The mixture is circulated using a gear pump, and the air entrapped is released using a V-notch valve. The oil and/or the thickeners are added until the required consistency is achieved. Presently, to check the consistency of the grease, the kettle stopped, and the sample is sent to a laboratory for testing via a so-called grease penetrometer device. This process is very time consuming and inefficient since adjustments have to be made during the manufacturing of the grease by adding oil and additives to reach the desired grease consistency, as indicated by a grade level specified by the National Lubricating Grease Institute (NLGI). It is taken care that, during the mixing the grease does not degrade.

In this example, two GDMU are used: one connected to the circulating pump and the other to the gear motor that drives the breaker bar units in the kettle. Monitoring units will measure and monitor the power and entropy in the process loop and within the kettle. It is postulated that the power consumed and entropy generated during the mixing of the mixture is proportional to the consistency of the grease, i.e., for a higher grade of grease, the power/entropy values are greater and vice-versa. Therefore, using the instantaneous values of power consumed by motor and pump and from the calculated entropy, the consistency of the grease mixture at time t is identified. The instantaneous power and entropy are determined using Eq. (8) and (9), respectively.

$$P(t) = V(I(t) - I_0)\cos\phi(t) \tag{8}$$

$$S(t) = V\frac{(I(t) - I_0)}{T(t)}\cos\phi(t) \tag{9}$$

Now, when a mixture is uniformly mixed, the values of power and entropy will be invariant with time i.e. change in the power and entropy values with time will be close to zero. Using this criteria, the uniform mixing of mixture is determined. Change in the power and entropy values with time, is determined using Eqs. (10) and (11) respectively.

$$\dot{P} = \frac{dP}{dt} = V\frac{d[(I(t) - I_0)\cos\phi(t)]}{dt} \approx 0 \tag{10}$$

$$\dot{S} = \frac{dS}{dt} = V\frac{d\left[\frac{(I(t) - I_0)\cos\phi(t)}{T(t)}\right]}{dt} \approx 0 \tag{11}$$

In case of a repeated mixture i.e. samples having the same ingredients in the same proportion, the time for uniform mixing can be determined by measuring the cumulative power and entropy. The cumulative power and entropy for change in wear mechanism or coating failure is constant. Similarly, the cumulative power $P_{cumm}$ and cumulative entropy $S_{cumm}$, to achieve uniform mixing is constant. The cumulative power and entropy is determined using Eqs. (12) and (13) respectively.

$$P_{cumm} = \int_0^t V(I(t) - I_0)\cos\phi(t)dt = C_1 \tag{12}$$

-continued $$S_{cumm} = \int_0^t \frac{V(I(t) - I_0)\cos\phi(t)}{T_i(t)} dt = C_2 \quad (13)$$

Figure 12:
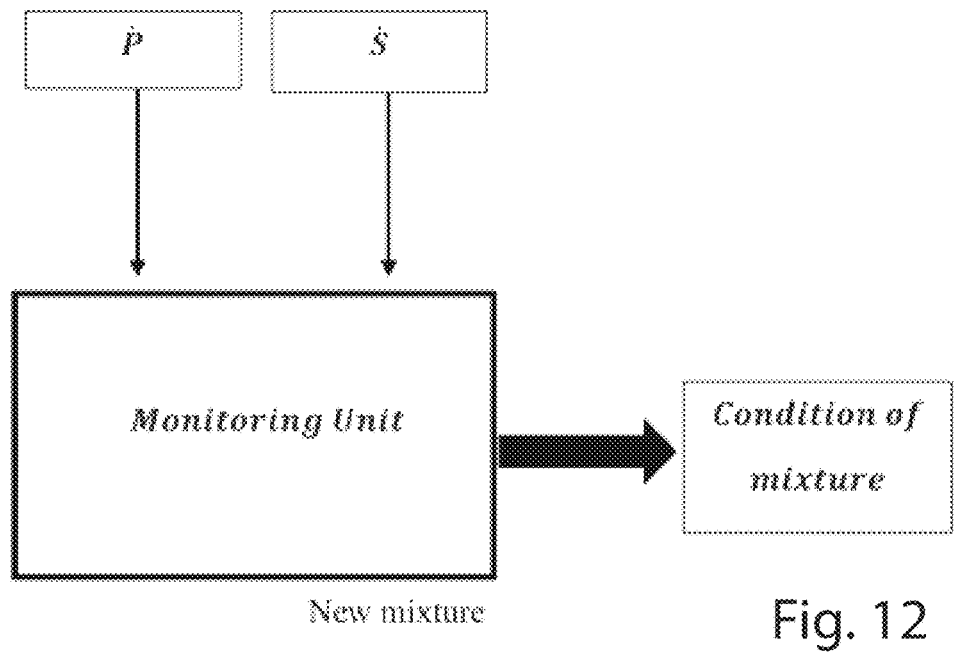
FIG. 12 depicts the usage of data to evaluate mixtures.

FIG. 12 summarizes that using the parameters: rate of change of power $\dot{P}$ and rate of change of entropy $\dot{S}$, the mixing condition for a new mixture can be determined.

Figure 13:
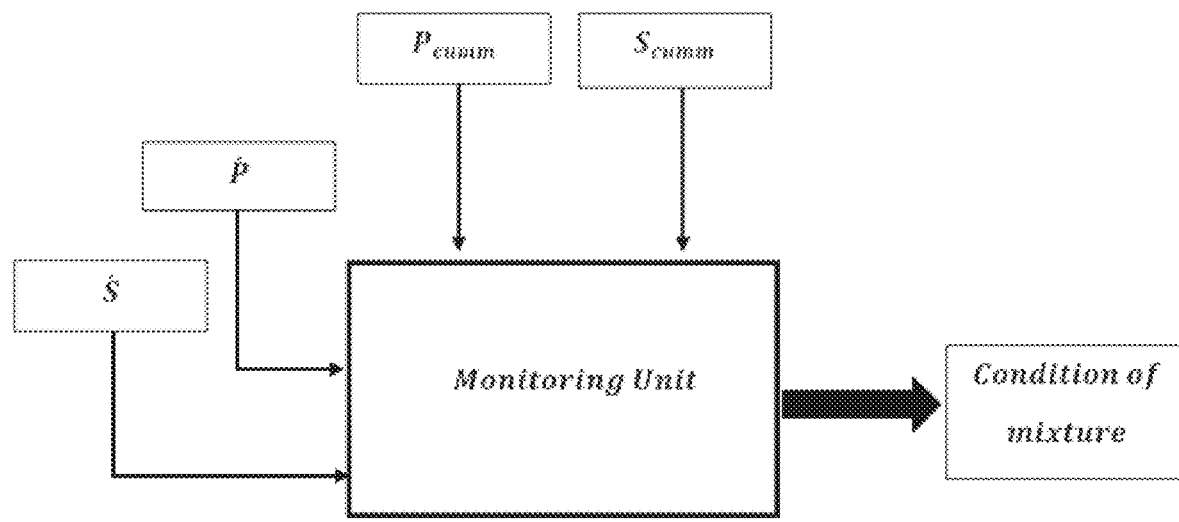
FIG. 13 depicts the usage of data to evaluate mixtures.

In case of mixing a known sample, the mixing condition can be determined from accumulated power $P_{cumin}$, accumulated entropy $S_{cumin}$, $\dot{P}$ and $\dot{S}$ as summarized in FIG. 13.

Soap Formation/Mixing Liquid

Figure 14:
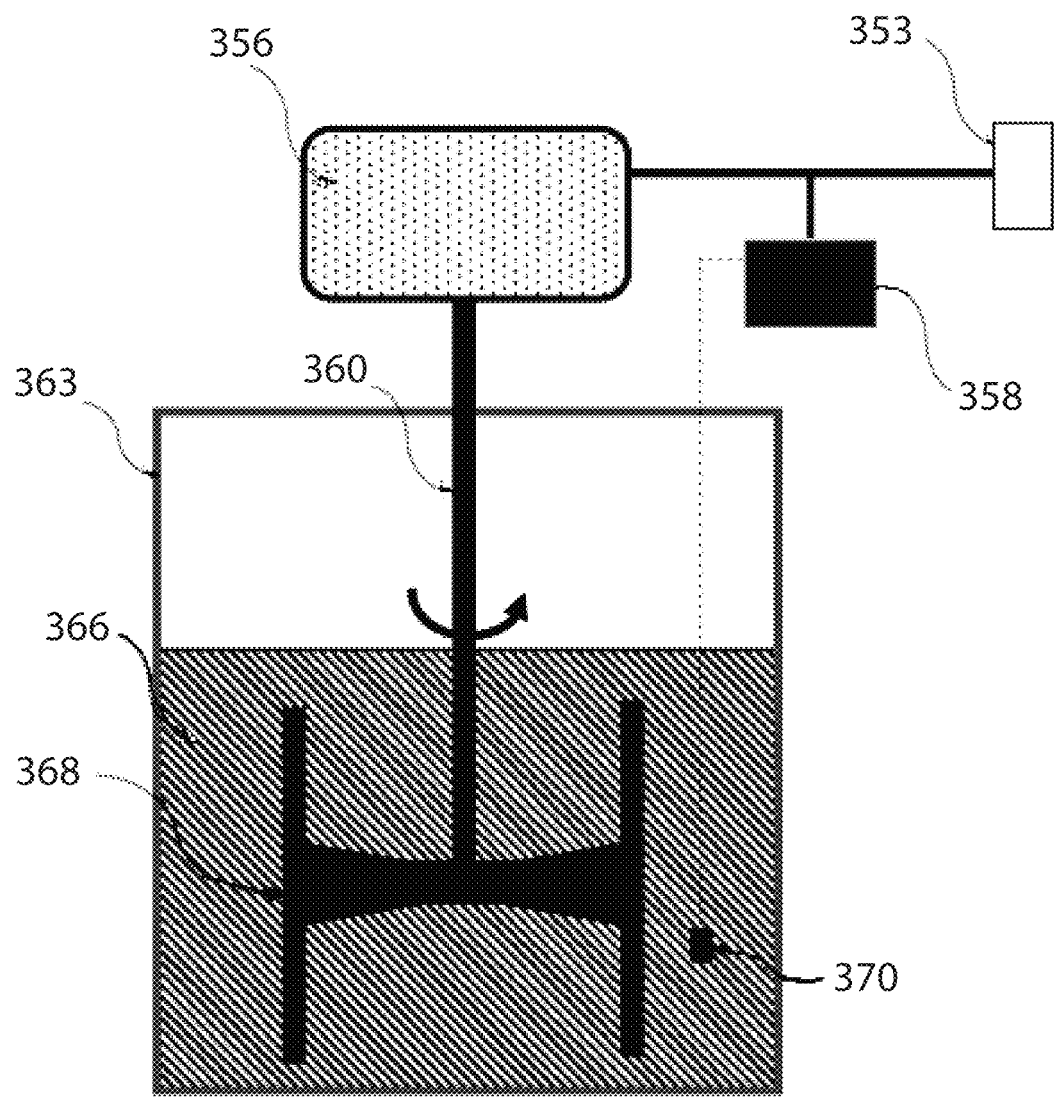
FIG. 14 depicts a mixing vessel.

Production of grease starts with a reaction-preparation phase where oil, acids, base and polymers (in some cases) are mixed in a vessel for developing the necessary grease soap. These ingredients are continuously mixed via rotating scrapers to form soap crystals. During this phase, the mixer's viscosity changes until it becomes steady when it reaches a plateau and the viscosity becomes uniform. The viscosity of the mixture is presently tested by stopping the operation and sending the samples to a laboratory for measuring the mixture's viscosity. For this purpose, the operation needs to be stopped several times, and samples taken to the lab and tested to determine the mixture viscosity. Now, by connecting the monitoring unit between the motor and power supply, the power consumed and/or entropy generation are measured. Power consumed is measured via the current drawn from the motor, and a temperature sensing device (e.g., a thermocouple) is used to measure the temperature necessary for determining the entropy. It is postulated that the power consumed/entropy generated by the mixture depends on the consistency of the mixture. When the process becomes steady, the grease viscosity becomes uniform, and the monitoring unit's output will indicate the completion of the process and send a notification signal and appropriate data to the user/operator. The equations used for grease kettles is used for evaluation. FIG. 14 shows a potential configuration of a vessel for forming soap or mixing liquids according to the present disclosure. The configuration may include power supply 353, motor 356, monitoring unit 358, rod 360, container 363, fluid mixture 366, scraper 368, and thermocouple 370.

In another example, the equilibrium consistency of the two mixing liquids is determined. Knowing the consistency of two mixing liquids having different consistency values will inform the practitioners to stop the mixing operation and proceed to the next step.

As illustrated before, the measured power and entropy values using the monitoring unit changes are directly proportional to the consistency of the liquid. Therefore, when liquids having two consistency grades are mixed, the power and entropy values change until consistency reaches an equilibrium. For example, if the consistency of the primary liquid is lower, upon adding a secondary liquid having a higher consistency, the power and entropy values will immediately increase and vary with mixing until the process becomes steady, indicating that a uniform mixing or equilibrium consistency has been reached. The equation used for grease kettles is used for evaluation.

Examples of mixing described herein may have particular utility when the resulting homogenous mixture has a consistency matching the standard for National Lubricating Grease Institute consistency grade 1, 2, or 3. Other examples of resulting homogenous mixtures may have a consistency matching the standard for National Lubricating Grease Institute consistency grades 0-4. Still other examples of resulting homogenous mixtures may have a consistency matching the standard for National Lubricating Grease Institute consistency grades 000-6.

Example Set 3

Bearings

Figure 15:
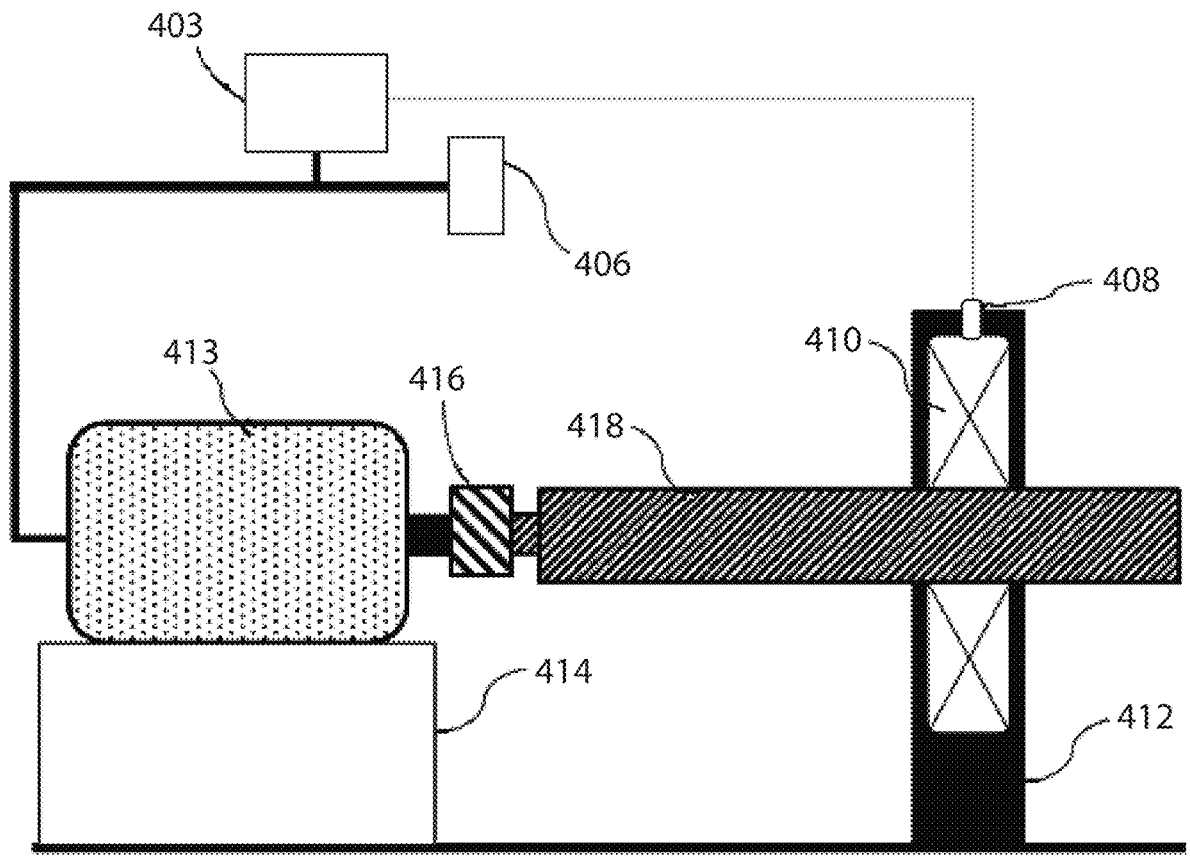
FIG. 15 depicts a bearing setup.

The usefulness of the proposed methodology for determining the condition of the grease in a bearing is illustrated in this example. An example bearing setup for monitoring is depicted in FIG. 15. That example setup may include a monitoring unit 403, a power supply 406, a thermocouple 408, a grease packed lubricant volume 410, a bearing casing 412, a motor 413, a motor support 414, a coupling 416, and a shaft 418. Here, by measuring the power consumed by the motor from the current, and voltage measured from the monitoring unit, and entropy generated by measuring the temperature. The degradation of grease with time can be determined by estimating the consistency of the bearing grease. The power and entropy values are proportional to grades of the grease, i.e., for a higher grade of grease, the power/entropy values are high and vice-versa.

One effective way of determining the consistency is by measuring their reduction in their NLGI grade level. Typically, a particular NLGI grade is specified for a bearing to operate smoothly and efficiently. During the bearing operation, the grease is sheared continuously causing physical/mechanical degradation where the grease breaks down and its consistency drops, jeopardizing the operation of the bearing. If no corrective action is taken, bearing failure becomes likely.

In this example, two different runs may be performed as a set. In case 1 the runs are conducted without grease and with different grades of grease and in case 2 the runs include grease. In Case 1, the setup is operated initially without grease and with several grades of greases for a range of operating conditions, and the readings of power and entropy generation are recorded and saved in a software library stored in the GDMU. In Case 2, the bearing is filled with the desired grease with the appropriate NLGI grade, and the experiment is performed. The time required for a grease of higher grade to degrade to the next level grade grease is determined using the in-build curve-fitting program in the monitoring device to inform the user/operator.

For example, let us consider an NLGI grease of Grade 2 used in actual application. Before performing the experiments, the setup is operated at lower grade greases: Grades 1, 0, and 00. The power and entropy values for different grades of greases are determined and saved in the software library. Now, the setup is operated with Grade 2 and their real-time values are recorded. Using the in-build program in the monitoring device, the time for the grease Grade of 2 to degrade to the power/entropy values of lower Grades 1, 0, and 00 are rapidly determined, by extrapolating the values. Thus, this procedure determines the useful life of the grease. Also, by comparing the real-time values of power/entropy and the library values, the level of degradation can be ascertained.

The procedure of determining the degradation of a liquid may proceed as follows. The setup is operated without any grease, the values of current ($I_0$) and contact temperature ($T_0$) values are recorded and saved in the library. Similarly, the setup is operated with different NLGI grades of grease, at a desired rotational speed, and once again the values of current and contact temperature values are recorded.

From the values of current and temperature, the power and entropy values are determined using Eqs. (8) and (9) respectively. The values of power and entropy for the greases having lower NLGI grade compared to the actual grease used for application, will be considered as threshold values as $P_t$ and $S_t$, respectively. These values are saved in the library of the monitoring device. The setup is operated at its actual operating conditions and the values of current and temperature may be recorded in real time. During the degradation of grease, the consistency of the grease constantly decreases with time. Now, considering the implementation of higher grade grease such as Grade 2 in the application, the values of power and entropy will constantly reduce with time and after certain time t the values will reach the threshold power and entropy values of its lower grade grease such as Grade 1 or 0 or 00. When the values cross the threshold values, an alarm may be sent to the user, for the grease replacement. The selection of the lower grade depends on the user. In the previous step, the instantaneous power and entropy may be continuously monitored. When the instantaneous values cross the threshold values, the grease is replaced. Instead of continuous monitoring of power and entropy values, a power curve fit equation may be used. It is based on the observation that the degradation of grease fits the power equation of the form given in Equations (14) and (15).

$$P = At^B + C \tag{14}$$

$$S = At^B + C \tag{15}$$

In this method, the setup may be operated with the actual grease and data is recorded for few minutes. The obtained values of power and entropy is curve fitted to the equation provided in Equations (14) and (15) and the values of coefficients A, B and C is determined using the regression method.

Using the values of coefficient, the time t is determined for the values of power and entropy to reach their threshold values $P_t$ and $S_t$, respectively. The value of t will provide an approximate time, after which the grease needs to be replaced.

Measuring through the power and entropy with the GDMU device does not require any modification in the existing setup. For example, when attaching a torque sensor between the bearing and motor, the shaft size needs to be reduced to incorporate a torque sensor and two couplings. Also, the torque sensor requires a data acquisition system to be attached to the power supply and the necessary software to obtain useful data from the torque sensor. The GDMU merely needs to wrap around the current-carrying wire, and the results may be transferred to the mobile app or email or sent directly to the control room in the plant.

As described herein, the unit referred to as the Grease Degradation Monitoring Unit or GDMU has a variety of uses and may be referred to more broadly as a "fluid monitoring unit" especially in those examples not involving grease. The methods described herein may have broad applicability across a range of industries. For example, the methods described herein may be used in the preparation of peanut butter.

Although greases of higher grades may have a reduced ability to conform to the shape of a container, all greases suitable for industrial lubrication are considered liquids as the term "liquid" is used herein. All materials having a consistency that would test at or below National Lubricating Grease Institute consistency grade 6 are also regarded as liquids for the purposes of this disclosure. This simplification removes the necessity of detailed discussion of the physical properties of numerous compositions which have consistencies at or below National Lubricating Grease Institute consistency grade 6. Accordingly, greases and other compositions of similar consistency would also be described as fluids herein.

Calculated quantities of power, including those in which voltage is multiplied by current to determine power, have the dimensional form $$\frac{mass * length^2}{time^3}.$$

Calculated quantities of entropy, including those in which voltage is multiplied by current and divided by temperature to determine entropy, have the dimensional form $$\frac{mass * length^2}{Temperature * time^3}.$$

Calculated quantities of rate of change of power ($\dot{P}$), including those in which voltage is multiplied by current to determine a rate of change of power, have the dimensional form $$\frac{mass * length^2}{time^4}.$$

Calculated quantities of rate of change of entropy ($\dot{S}$), including those in which voltage is multiplied by current and divided by temperature to determine a rate of change of entropy, have the dimensional form $$\frac{mass * length^2}{Temperature * time^4}.$$

Calculated quantities of cumulative power ($P_{cumm}$) including those in which voltage is multiplied by current to determine a cumulative power, have the dimensional form $$\frac{mass * length^2}{time^2}.$$

Calculated quantities of cumulative entropy ($S_{cumm}$) including those which voltage is multiplied by current: and divided by temperature to determine a cumulative entropy, have the dimensional form $$\frac{mass * length^2}{Temperature * time^2}.$$

The above-described embodiments have a number of independently useful individual features that have particular utility when used in combination with one another including combinations of features from embodiments described separately. There are, of course, other alternate embodiments which are obvious from the foregoing descriptions, which are intended to be included within the scope of the present application.

The invention claimed is:

1. A method of evaluating mixing comprising:
   a. combining a first material with a second material thereby creating a first mixture wherein the first mixture is initially a non-homogenous mixture;
   b. operating a motor to work the first mixture with a first implement;
   c. measuring a first current to the motor;
   d. recording a first current data set representing values of the first current over time;
   e. calculating a rate variable using the first current dataset wherein the rate variable has a first dimensional form selected from:

$$\frac{\text{mass} * \text{length}^2}{\text{time}^4} \text{ and } \frac{\text{mass} * \text{length}^2}{\text{Temperature} * \text{time}^4};$$

and
   f. turning off the motor after the rate variable reaches a first threshold value.

2. The method of claim 1 further comprising:
   a. calculating a cumulative variable using the first current dataset wherein the cumulative variable corresponds with a cumulative working of the first mixture with the first implement and wherein the cumulative variable has a second dimensional form selected from:

$$\frac{\text{mass} * \text{length}^2}{\text{time}^2} \text{ and } \frac{\text{mass} * \text{length}^2}{\text{Temperature} * \text{time}^2};$$

b. wherein the turning off the motor occurs after the cumulative variable reaches a second threshold value.

3. The method of claim 1 wherein the calculating the rate variable occurs according to the formula $$\dot{P} = \frac{dP}{dt} = V \frac{d[(I(t) - I_o)\cos\phi(t)]}{dt}$$

wherein V is voltage, I(t) is time dependent current, $I_0$ is the current without grease, and $\phi(t)$ is a time dependent phase angle between the voltage and current.

4. The method of claim 1 wherein the calculating the rate variable occurs according to the formula $$\dot{S} = \frac{dS}{dt} = V \frac{d\left[\frac{(I(t) - I_0)\cos\phi(t)}{T(t)}\right]}{dt}$$

wherein V is voltage, I(t) is time dependent current, $I_0$ is the current without grease, $\phi(t)$ is a time dependent phase angle between the voltage and current, and T(t) is time dependent temperature.

5. The method of claim 1 further comprising the step of evaluating which portion of the first current is attributable to working the first mixture.

6. The method of claim 1 wherein the first mixture is a homogenous mixture having a National Lubricating Grease Institute consistency grade of at least 000 and at most 6 when the rate variable reaches the first threshold value.

7. The method of claim 1 wherein the first material is a lubricant.

8. The method of claim 1 wherein the first material is an oil.

9. The method of claim 1 wherein the first material is a grease.

10. The method of claim 1 wherein the first mixture is circulated with a gear pump.

11. The method of claim 1 wherein a temperature sensing instrument measures a temperature of the first mixture and a second data set representing the temperature of the first mixture is recorded.

12. The method of claim 1 wherein the first implement is a scraper.

13. A method of evaluating lubricant degradation comprising:
   a. filling a lubrication fill space of a mechanical device with a first volume of a first grease wherein the first grease has a first grease grade;
   b. wherein the first grease grade matches a lower threshold for the operation of the mechanical device indicative of a reduced level of protection for the mechanical device;
   c. running a motor thereby working the first volume of the first grease;
   d. measuring a first current to the motor associated with the first volume of the first grease;
   e. filling the lubrication fill space of the mechanical device with a second volume of a second grease wherein the second grease has a second grease grade that is higher than the first grease grade;
   f. running the motor thereby working the second volume of the second grease;
   g. collecting a series of current measurements to the motor indicating a change in current over time while the motor works the second volume of the second grease;
   h. curve fitting a comparison variable that is based on the series of current measurements to a first equation of the form:

$X = At^B + C$ wherein X is the comparison variable, wherein A is a first coefficient determined by the curve fitting, wherein B is a second coefficient determined by the curve fitting, wherein C is a third coefficient determined by the curve fitting, and wherein t is time;
   i. finding a value of the comparison variable associated with the first current; and
   j. evaluating a threshold time by solving the first equation using the value of the comparison variable associated with the first current, the first coefficient, the second coefficient, and the third coefficient.

14. The method of claim 13 further comprising changing the second volume of the second grease based on the threshold time.

15. The method of claim 13 wherein the comparison variable is a measure of electrical current.

16. The method of claim 13 wherein the comparison variable is a measure of power.

17. The method of claim 13 wherein the comparison variable is a measure of power and is calculated as $P(t) = V(I(t) - I_0)\cos\phi(t)$ wherein V is voltage, I(t) is time dependent current, $I_0$ is current without grease, and ϕ(t) is a time dependent phase angle between the voltage and current.

18. The method of claim 13 wherein the comparison variable is a measure of entropy.

19. The method of claim 13 wherein the comparison variable is a measure of entropy and is calculated as:

$$S(t) = V \frac{(I(t) - I_0)}{T(t)} \cos\phi(t)$$

wherein V is voltage, I(t) is time dependent current, $I_0$ is current without grease, T(t) is time dependent temperature, and ϕ(t) is a time dependent phase angle between the voltage and current.

* * * * *